US007356123B2

(12) United States Patent
Mollus

(10) Patent No.: US 7,356,123 B2
(45) Date of Patent: Apr. 8, 2008

(54) X-RAY DEVICE HAVING A COLLIMATOR, AND METHOD OF SETTING THE LATTER

(75) Inventor: Sabine Mollus, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 288 days.

(21) Appl. No.: 10/545,057

(22) PCT Filed: Feb. 4, 2004

(86) PCT No.: PCT/IB2004/000271

§ 371 (c)(1),
(2), (4) Date: Aug. 10, 2005

(87) PCT Pub. No.: WO2004/071303

PCT Pub. Date: Aug. 26, 2004

(65) Prior Publication Data

US 2006/0104420 A1    May 18, 2006

(30) Foreign Application Priority Data

Feb. 11, 2003    (EP) .................................. 03100277

(51) Int. Cl.
*G21K 1/02*    (2006.01)
(52) U.S. Cl. .......................... 378/147; 378/108; 378/62

(58) Field of Classification Search .................. 378/64, 378/65, 97, 108, 117, 207, 62, 98.5, 145, 378/147, 150, 204
See application file for complete search history.

(56) References Cited

U.S. PATENT DOCUMENTS

| 5,307,396 A | 4/1994 | Tsuchino |
| 5,332,908 A | 7/1994 | Weidlich |
| 6,292,537 B1 | 9/2001 | Zimmermann |
| 6,480,570 B1 | 11/2002 | Ikeda |
| 7,190,763 B2 * | 3/2007 | Mungilwar .................. 378/97 |

FOREIGN PATENT DOCUMENTS

DE    199 03 749 A1    8/2000

* cited by examiner

*Primary Examiner*—Courtney Thomas

(57) ABSTRACT

The present application relates to an X-ray device having an X-ray radiation source (7), a collimator (6) and an X-ray detector (4). The reduction in the radiation dose to which a patient (5) is exposed, said reduction being generated by the collimator (6), is calculated by a data processing unit (2) from the current setting of the shield and filter elements of the collimator (6) and displayed on a display unit (3), for example, as an area shielding factor AA and/or a dose reduction factor DRF. The user can in this way detect the potential of the collimator that still exists for image improvement and for minimizing the exposure to radiation.

20 Claims, 1 Drawing Sheet

X-RAY DEVICE HAVING A COLLIMATOR, AND METHOD OF SETTING THE LATTER

Figure 1:
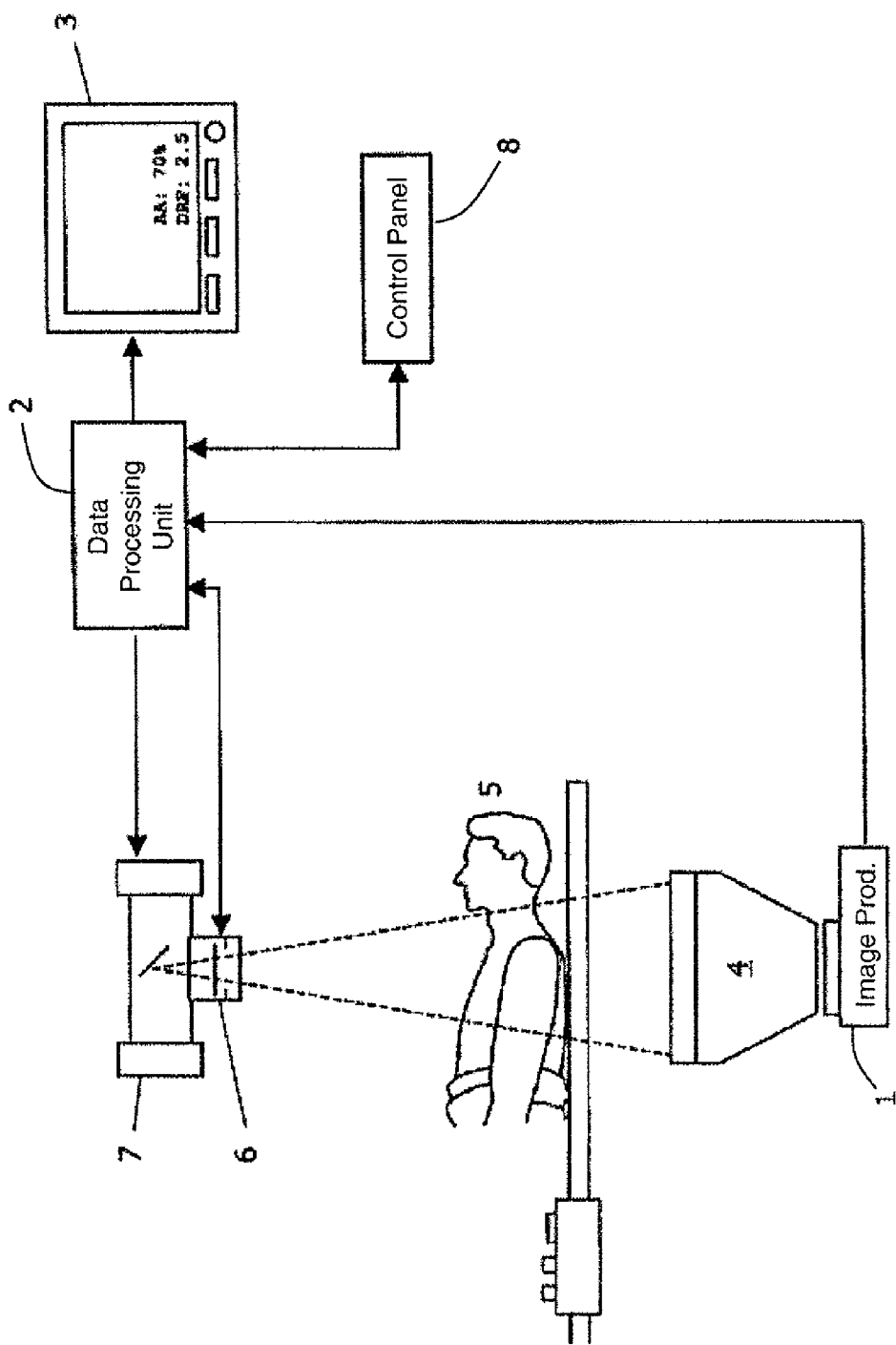

The invention relates to an X-ray device having a collimator, and also to a method of setting such a collimator.

X-ray devices for recording medical X-ray images usually comprise a collimator having non-transparent shutters and semi-transparent shielding wedges, setting of which allows the bundle of X-rays to be formed such that only parts of interest of the body of a patient are irradiated at the desired radiation intensity. Furthermore, collimators typically comprise filter elements for changing the spectrum of the ray in the desired manner. The most important advantages of using a collimator are the improvement in image quality, the decrease in the risk of damaging a patient by means of radiation (e.g. injuries to the skin) and the reduction in the scattered radiation to which the personnel are exposed during recording of the image.

U.S. Pat. No. 6,292,537 discloses an X-ray device having a collimator in which the effective dose to which the patient is exposed, taking account of the biological effectiveness of the radiation, is calculated as a function of the selected shield setting and the irradiated organ of the patient. It is hereby possible for the physician to more precisely assess the effects of the X-ray irradiation of various regions of the patient's body, so that he can better ensure, for example by setting the collimator, that predefined maximum doses are not exceeded.

Based on this, it is an object of the present invention to provide means which make it possible to further optimize the setting of a collimator.

This object is achieved by an X-ray device having the characteristic features of claim 1 and by a method having the characteristic features of claim 5. Advantageous versions are given in the subclaims.

The X-ray device according to the invention, which can in particular be used to generate medical X-ray images, comprises the following elements:

a) An X-ray radiation source, which typically comprises an X-ray tube for generating a bundle of X-rays.

b) A (manually or automatically) settable collimator having shield elements which are non-transparent and/or semi-transparent for X-ray radiation, by means of which shield elements a bundle of X-rays leaving the X-ray radiation source can be limited in terms of their shape and/or locally damped, and/or having filter elements, by means of which filter elements the spectrum of the X-ray can be changed. Typically, the shield elements include a so-called iris for the circular limiting of the bundle of X-rays and the filter elements include a radiation filter or prefilter system for optimizing the radiation quality.

c) An X-ray detector which is arranged in the path of the bundle of X-rays and which can measure, in a locally resolved manner, the amount of X-ray radiation striking it, where an examination object, for example a patient, is generally to be arranged between X-ray radiation source and X-ray detector.

d) Means for detecting, in the bundle of X-rays, the reduction in the radiation dose brought about by the collimator.

Such an X-ray device has the advantage that it provides the user with information as to how much the X-ray radiation leaving the X-ray radiation source is reduced by the collimator. This allows the user to better assess the potential that still exists or has already been used in the setting of the collimator for image improvement and for minimizing the exposure to radiation for the patient and the personnel. The collimator can thus better be optimally set with the aid of this information.

The reduction in the radiation dose brought about by the collimator can be measured directly, for example by appropriate sensors between the collimator and the patient. Preferably, the X-ray device comprises a data processing unit for controlling the generation of images and for processing recorded X-ray images, where the data processing unit is connected to the X-ray radiation source, the collimator and the X-ray detector and is set up for the purpose of detecting the current setting of the collimator and determining therefrom the reduction in the radiation dose brought about by the collimator. By knowing the current setting of the collimator, that is to say in particular the geometric positions and the absorption behavior of the individual shield and filter elements, the reduction in the radiation dose can be determined with a great deal of accuracy on account of theoretical estimates, without additional measurement being required. The current setting of the collimator may for example be measured by appropriate (position) sensors. If the data processing unit is set up to generate or pass on commands for an automatic setting mechanism of the collimator, the setting of the collimator can be deduced from the transmitted commands (even without sensor back-coupling). Furthermore, the position of the shield elements can also be determined from the recorded X-ray image by means of suitable methods of automatic image processing.

According to an improvement of the X-ray device, the latter comprises a display unit for displaying a recorded X-ray image and/or a display unit for displaying imaging parameters such as, for example, the generator voltage of the X-ray radiation source, where the detected reduction in the radiation dose can be displayed on said display units as text and/or as graphics. Display units for the X-ray image and for imaging parameters are generally present anyway in conventional X-ray devices. Therefore, it is proposed to display, on these display units, the determined reduction in the radiation dose as additional information for the user, so that he can use this when setting the collimator.

The invention furthermore relates to a method of setting the collimator of an X-ray device which may in particular be an X-ray device of the type mentioned above. In the method, based on the current setting of the collimator and possibly the setting of other components of the X-ray device, the reduction in the radiation dose brought about by the collimator is determined and displayed to the user. The reduction brought about may in this case optionally be expressed as an absolute value or as a ratio of the value of a parameter given the current collimator setting to the value of this parameter when the shield is completely opened and/or without filters. The method has the advantage, discussed above in relation to the X-ray device, that the user is given information about the still existing or already used optimization possibilities of the collimator. In particular, if other values such as the dose rate supplied to the patient or the overall dose of radiation (with or without the biological effectiveness being taken into account) already lie within target ranges, by means of the method a possibly as yet unused potential for further reducing the radiation dose can be detected and then used.

There are various possibilities for quantifying the reduction in the radiation dose brought about by the collimator. According to a first preferred method, the reduction in the radiation dose is quantified without dosimetry by the ratio of the cross-sectional areas of the bundle of X-rays (reaching the patient) with positioned shield elements in the collimator and without shield elements (that is to say with fully opened shields). According to a second preferred method, the reduction in the radiation dose is quantified by the ratio of the area dose products with and without positioning of the shield and filter elements in the collimator. The area dose product is a dosimetric value which corresponds to the product of the dose within the bundle of X-rays and its cross-sectional area at the same point (unit: $Gy \cdot cm^2$).

According to an improvement of the above method, the area dose product in the case of a set collimator is calculated as a function of characteristics of the X-ray radiation source of the X-ray device, such as its radiation quality (spectrum of the ray) for example. This allows more accurate determination of the reduction in the radiation dose in the case where filters and/or semi-transparent shield elements such as wedges with a continually increasing thickness, for example, are used, in which the amount of radiation which gets through is dependent on the radiation quality of the incident radiation.

The determined reduction in the radiation dose is preferably displayed as text (e.g. numerical value) and/or as graphics (e.g. pie chart or bar chart) in order that the user can make use thereof. Furthermore, the reduction in dose brought about by different elements, e.g. by the shield elements on the one hand and the filter elements on the other, can be displayed separately. In this respect, a combined display using color coding of the proportions of dose reduction is also conceivable.

According to another improvement of the method, the reduction in back-scattering of the X-ray radiation and/or the improvement in image quality is determined from the reduction in the radiation dose and displayed to the user. In this way, the user can directly detect the used and still existing potential for positive effects of the dose reduction.

The invention will be further described with reference to examples of embodiments shown in the drawing to which, however, the invention is not restricted.

The sole FIGURE schematically shows the components of an X-ray device according to the invention.

In order to generate an X-ray image of the body of a patient 5, the X-ray device comprises an X-ray radiation source 7 having an X-ray tube, which generates X-ray radiation using the X-ray voltage supplied by a generator, and an X-ray detector 4, which in a locally resolved manner measures the X-ray radiation which the body of the patient 5 lets through. The X-ray detector 4 is furthermore connected to an image production unit 1 for reading the individual image sensors. The X-ray device and the processing of the (digitized) X-ray images obtained are controlled by a data processing unit 2 which is connected for this purpose to the image production unit 1 and the X-ray radiation source 7. Furthermore, the data processing unit 2 is connected to a system control panel 8, by means of which a user can input commands and control the recording procedure, and to a display unit 3 for displaying the recorded X-ray image.

The X-ray device furthermore comprises a collimator 6, of which two shutters penetrating into the bundle of X-rays and one filter are shown by way of representation in the FIGURE. The collimator also includes a so-called primary radiation filter (not shown) comprising an iris, which of the radiation generated by the X-ray tube lets through only a cone-shaped bundle of rays, and a prefilter. Radiation filters in the collimator are frequently used to control the radiation quality and to reduce the patient dose.

The collimator 6 is likewise connected to the data processing unit 2, it being possible for the latter to transmit commands for setting desired positions of the filter and shield elements to the collimator 6, where said commands are executed by an appropriate automatic positioning mechanism.

The information available to the users in the prior art for setting a collimator is the overall patient dose (unit: $Gy \cdot cm^2$) and momentary patient dose rate (unit: $cGy \cdot cm^2/s$), which are determined while taking into account only the shutters and the iris position, and the trimming of the current image which is generated by the shields. By closing the shields of the collimator as far as possible, the image quality can be improved on account of the reduction in scattered radiation. Furthermore, the exposure of the patient and also of the personnel to radiation is also minimized. Despite these advantages, in clinical practice collimators are used only sporadically.

In order to better inform the user of an X-ray device having a collimator, the detection of the reduction in the radiation dose brought about by the collimator is therefore carried out according to the invention. Preferably, this reduction is in this case calculated on the basis of theoretical considerations from the current setting of the collimator and of the X-ray device as a whole. Said settings include, for example, the positions and transmission functions of the shield and filter elements. In an auxiliary aspect of the method, it is also possible to assess the benefit for personnel on account of the reduced back-scattering or the benefit for image quality.

Various dosimetric parameters can be used for visualizing the dose reduction, e.g. the energy dose (unit: Gray), the ion dose (kerma: "kinetic energy released in matter") or the effective dose or equivalent dose (unit: Sievert). The latter may for example be calculated from a patient model by determining the patient section image from the detector image and automatically segmenting various tissue types (e.g., U.S. Pat. No, 6,292,537). In the dose determination, a distinction is further made between the patient entry dose (pure dose without scattered portion) and the surface dose (with scattering being taken into account). In principle, both absolute information (e.g. dose rate of the area dose product in $cGy \cdot cm^2/s$ or integral area dose product in $Gy \cdot cm^2$) and relative information (see below) can be obtained.

Specifically, the use of the X-ray device in the method according to the invention is, for example, as follows:

First, the filter and shield elements of the collimator 6 are positioned manually by the operator using the control panel 8 or automatically by the data processing unit 2. The positions of the shield elements are then read by the data processing unit 2 in order to calculate therefrom the shielded cross-sectional area $A_b$ of the bundle of X-rays (that is to say the area which is "missing" behind the collimator 6). The area shielding factor AA can then be calculated as a quotient of the shielded cross-sectional area $A_b$ and of the overall cross-sectional area $A_0$ of the bundle of X-rays when the shield is open, in accordance with:

$$AA = \frac{A_b}{A_0} \cdot 100\%$$

Thus, a value of AA=0% corresponds to a completely open shield, and a value of AA=100% corresponds to a completely closed shield. Depending on the basic use, the momentary image must still be analyzed in order to exclude non-relevant areas with direct irradiation (that is to say without the X-ray radiation passing through the patient) from these calculations. In such an analysis, for example, first a simulated threshold value of the image brightness without absorption (or with only a few centimeters of water absorption) is determined as a function of the given acquisition parameters (X-ray tube voltage and current, prefiltering, II mode, spectrum, etc.); segmenting then takes place, in which image areas which are brighter than the threshold value are classified as areas of direct radiation and image areas which are darker than the threshold value are classified as patient-relevant areas.

Furthermore, the setting values of the current generator of the X-ray radiation source 7 can be used to determine the filter transmission in the collimator 6, said filter transmission being dependent on the radiation quality. In this way, the dose reduction factor DRF can be calculated. In this case, the area dose product per image, per second, per sequence or per intervention with a completely opened shield, $DAP_0$, is placed in relation with the assessed area dose product after placement of the filters, $DAP_b$, in accordance with $$DRF = \frac{DAP_0}{DAP_b}$$

Alternatively, the relative reduction DR in the area dose product can also be calculated in accordance with $$DR = \frac{DAP_b}{DAP_0} \cdot 100\%$$

The abovementioned parameters of the area shielding factor AA, the relative reduction in the area dose product DR and/or the dose reduction factor DRF may be displayed as special indicators. Conventional X-ray systems visualize the patient dose on the system control panel 8 and on a display unit 3 below the current X-ray image. The last-mentioned display unit typically comprises information about various imaging parameters (SID=Source-Image-Distance, current charge of the tube, II mode, patient dose rate, etc.). The new indicator for the dose reduction can be displayed either on the display unit 3 or on the display unit 3 and the system control panel 8.

There are various possibilities for the representation of the data. In the simplest case, as shown in the FIGURE, the absolute numerical value of the indicators can be displayed. In addition or as an alternative, it is also possible for a symbolic representation to be selected, such as a pie chart or bar graph for example.

The above-described new indicator for the reduction in the radiation dose by the collimator 6 is particularly valuable in connection with approaches for automatic filter placement and for imaging of a region of interest, since it makes the advantages of automatic filter placement directly discernible. In connection with manually set collimators, the new indicator provides the user with more information about the available potential for dose reduction, so that the latter can in practice be used on a more regular basis with corresponding advantages for the image quality and for minimizing the exposure to radiation.

The invention claimed is:

1. An X-ray device comprising:
 an X-ray source;
 a settable collimator;
 an X-ray detector; and
 a data processing unit which calculates a reduction in radiation dose brought about by the collimator.

2. The X-ray device of claim 1 further comprising a display unit for displaying the calculated reduction in radiation dose.

3. The X-ray device of claim 2 wherein the reduction in the radiation dose is quantified by the ratio of the radiation cross-sectional areas with and without the collimator.

4. The X-ray device of claim 2 wherein the reduction in the radiation dose is quantified by the ratio of the area dose products with and without the collimator.

5. The X-ray device of claim 1, wherein the data processing unit calculates the reduction in the radiation dose (DR) by using the relationship:

$$DR = DAP_b/DAP_0 \cdot 100\%$$

where $DAP_b$ is an area dose product with filters in place, and $DAP_0$ is an area dose product with a completely open shield.

6. The X-ray device of claim 2, further including:
 an imaging region for receiving a subject to be imaged;
 a reconstruction processor that reconstructs received x-rays into an image representation of the subject, wherein the display unit displays the image representation and the reduction in dose concurrently.

7. An X-ray device, comprising:
 a) an X-ray radiation source;
 b) a settable collimator for limiting, locally damping and/or filtering a bundle of X-rays;
 c) an X-ray detector; and
 d) means for detecting a reduction in the radiation dose brought about by the collimator.

8. An X-ray device as claimed in claim 7, further comprising a data processing unit for controlling the generation of images and for processing recorded X-ray images, which data processing unit is connected to the X-ray radiation source, the collimator and the X-ray detector and is set up for the purpose of detecting the current setting of the collimator and determining therefrom the reduction in the radiation dose brought about by the collimator.

9. An X-ray device as claimed in claim 7, further comprising a display unit for displaying a recorded X-ray image, and displaying the detected reduction in the radiation dose as text and/or as graphics.

10. An X-ray device as claimed in claim 7, further comprising a display unit for displaying imaging parameters, and displaying the radiation dose as text and/or as graphics.

11. An x-ray device as claimed in claim 7, wherein the collimator includes a shutter, and iris for limiting cross-sectional area of an x-ray beam from the x-ray source, and filter elements with adjustable x-ray transparency for adjusting a spectrum of the x-rays.

12. A method of setting the collimator of an X-ray device, wherein, based on the current setting of the collimator and possibly other components of the X-ray device, the reduction in the radiation dose brought about by the collimator is determined and displayed.

13. A method as claimed in claim 12, wherein the reduction in the radiation dose is quantified by the ratio of the radiation cross-sectional areas with and without the collimator.

14. A method as claimed in claim 12, wherein the reduction in the radiation dose is quantified by the ratio of the area dose products with and without the collimator.

15. A method as claimed in claim 14, wherein the area dose product with collimator is calculated as a function of characteristics of the X-ray radiation source of the X-ray device.

16. A method as claimed in claim 12, wherein the reduction in the radiation dose is displayed as text and/or as graphics.

17. A method as claimed in claim 12, wherein the reduction in back-scattering of the X-ray radiation and/or the improvement in image quality is determined from the reduction in the radiation dose.

18. A method as claimed in claim 12, wherein the radiation dose reduction is displayed during a patient examination to indicate the reduction in radiation dose in real time during the examination.

19. A method as claimed in claim 16, further including:
disposing a subject in an imaging region of the x-ray device;
reconstructing received x-rays into an image representation;
displaying the image representation and the reduction in dose concurrently.

20. The method of claim 12, wherein the step of determining the radiation dose (DR) brought about by the collimator includes using the relationship:

$$DR = DAP_b/DAP_0 \cdot 100\%$$

where $DAP_b$ is an area dose product with filters in place, and $DAP_0$ is an area dose product with a completely open shield.

* * * * *